United States Patent

Lind et al.

[11] 4,163,007
[45] Jul. 31, 1979

[54] NEW STABILIZERS

[75] Inventors: Hanns Lind, Füllinsdorf; Paul Moser, Riehen, both of Switzerland

[73] Assignee: Ciba-Geigy Corporation, Ardsley, N.Y.

[21] Appl. No.: 819,526

[22] Filed: Jul. 27, 1977

[30] Foreign Application Priority Data

Jul. 30, 1976 [CH] Switzerland ............... 9764/76

[51] Int. Cl.² .................... C08K 5/52; C07F 7/22; C07F 9/02
[52] U.S. Cl. .................... 260/45.75 R; 8/180; 260/45.75 G; 260/45.75 M; 260/45.75 N; 260/45.75 W; 260/45.75 T; 260/45.85 R; 260/429 R; 260/429.7; 260/429.9; 260/438.5 R; 260/439 R; 260/448 R; 260/940; 260/941
[58] Field of Search ............ 260/45.75, 45.85 T, 260/45.9 KA, 429, 429.7, 439, 940, 941; 8/180

[56] References Cited

U.S. PATENT DOCUMENTS

| | | | |
|---|---|---|---|
| 3,112,338 | 11/1963 | Smutny et al. | 260/45.85 B |
| 3,189,630 | 6/1965 | Smutny | 260/45.75 N |
| 3,310,575 | 3/1967 | Spivack | 260/45.75 R |
| 3,491,024 | 1/1970 | Kujawa et al. | 260/45.7 PH |
| 3,763,287 | 10/1973 | Chiddix et al. | 260/941 |
| 3,920,712 | 11/1975 | Spivack et al. | 260/45.75 N |

Primary Examiner—V. P. Hoke
Attorney, Agent, or Firm—Vincent J. Cavalieri

[57] ABSTRACT

The invention relates to compounds of the general formula I

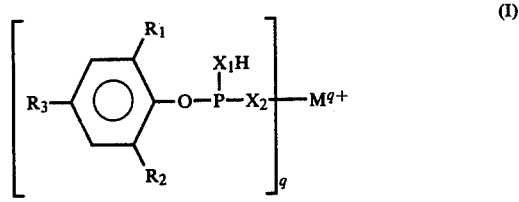

(I)

wherein
$R_1$ and $R_2$ independently of one another are $C_1$-$C_8$-alkyl, $C_5$-$C_8$-cycloalkyl or $C_7$-$C_9$-aralkyl,
$R_3$ is —CN or a group either of the formula II or III

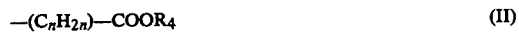

$$-(C_nH_{2n})-COOR_4 \quad (II)$$

or

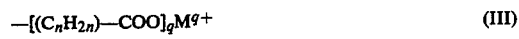

$$-[(C_nH_{2n})-COO]_qM^{q+} \quad (III)$$

wherein n is 0 to 6,
$R_4$ is $C_1$-$C_{24}$-alkyl, phenyl, or alkyl-substituted phenyl having 1-12 C atoms in the alkyl moiety,
q is 1, 2 or 3,
$M^{q+}$ is $H^+$ or a mono-, bi- or trivalent metallic cation, and
$X_1$ and $X_2$ are —O— or —S—, which are suitable as antioxidants and light stabilizers for organic material.

7 Claims, No Drawings

NEW STABILIZERS

The present invention relates to new sterically hindered esters of phosphorous acid and to salts thereof, to their production, to their use as antioxidants and light stabilisers and to plastics stabilised by the use thereof.

The use of sterically hindered phosphites as antioxidants in polyolefins is known for example from U.S. Pat. No. 3,491,024. Phosphites can also be used together with conventional light stabilisers, such as benzophenones or benztriazoles, in order to impart to the polymer to be protected a certain stability to light. It has not been possible hitherto to use phosphites on their own as light stabilisers on account of inadequate effectiveness.

There has now been found a class of primary phosphites which surprisingly can be used not only as antioxidants but also as light stabilisers in plastics. The new compounds correspond to the general formula I

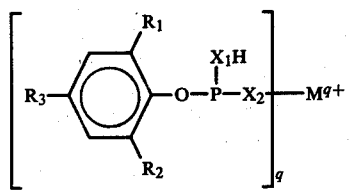

wherein
$R_1$ and $R_2$ independently of one another are $C_1$–$C_8$-alkyl, $C_5$–$C_8$-cycloalkyl or $C_7$–$C_9$-aralkyl,
$R_3$ is —CN or a group either of the formula II or III $$-(C_nH_{2n})-COOR_4 \qquad (II)$$

or $$-[(C_nH_{2n})-COO]_qM^{q+} \qquad (III)$$

wherein n is 0 to 6,
$R_4$ is $C_1$–$C_{24}$-alkyl, phenyl, or alkyl-substituted phenyl having 1–12 C atoms in the alkyl moiety,
q is 1, 2 or 3,
$M^{q+}$ is $H^+$ or a mono-, bi- or trivalent metallic cation, and
$X_1$ and $X_2$ are —O— or —S—, As $C_1$–$C_8$-alkyl, $R_1$ and $R_2$ are for example methyl, ethyl, isopropyl, t-butyl, α,α-dimethylbutyl, α-methylhexyl or t-octyl; preferred groups however are α-branched alkyl groups having 4–8 C atoms.

Examples of $R_1$ and $R_2$ as $C_5$–$C_8$-cycloalkyl are cyclopentyl, cyclohexyl or cyclooctyl. As $C_7$–$C_9$-aralkyl, $R_1$ and $R_2$ are for example benzyl, α-phenylethyl or α,α-dimethylbenzyl. The symbol n denotes 0 to 6; particularly preferred however are compounds in which n is 0. $R_4$ as $C_1$–$C_{24}$-alkyl is for example methyl, ethyl, n-propyl, isopropyl, n-butyl, n-octyl, n-decyl, n-dodecyl, n-octadecyl, n-docosyl or n-tetracosyl. As alkyl-substituted phenyl, $R_4$ is for example 2,4-di-t.-butylphenyl, 4-t.-butylphenyl, 2,4-dimethylphenyl or 2,6-dimethyl-4-t.-butylphenyl. As a metallic cation, $M^{q+}$ can be any mono- bi- or trivalent metal cation. Alkali metal cations, alkaline-earth metal cations, heavy cations and transition cations are suitable for forming salts. Preferred for practical reasons are $Na^{30}$, $K^+$, $Mg^{2+}$, $Ca^{2+}$, $Cr^{3+}$, $Co^{2+}$, $Ni^{2+}$, $Zn^{2+}$, $Al^{3+}$ and $Sn^{2+}$. To be emphasised among these are particularly $Ca^{2+}$, $Co^{2+}$, $Ni^{2+}$ and $Zn^{2+}$.

Primary phosphites of the formula I preferably used are those wherein $R_1$ and $R_2$ independently of one another are $C_4$–$C_8$-alkyl, and $R_3$ is a group either of the formula II or III in which n is 0 to 3, and $R_4$ is $C_1$–$C_{18}$-alkyl, phenyl, or alkylsubstituted phenyl having 1 to 8 C atoms in the alkyl moiety, and q is 1, 2 or 3, and $M^{q+}$ is $H^+$, $Na^+$, $K^+$, $Mg^{2+}$, $Ca^{2+}$, $Cr^{3+}$, $Co^{2+}$, $Ni^{2+}$, $Zn^{2+}$, $Al^{3+}$ or $Sn^{2+}$, and $X_1$ and $X_2$ are —O—.

Compounds of the formula I to be especially emphasised are those wherein $R_1$ and $R_2$ independently of one another are $C_4$-alkyl or $C_8$-alkyl, and $R_3$ is a group either of the formula II or III wherein n is 0 to 2, and $R_4$ is $C_1$–$C_{18}$-alkyl, phenyl, or alkyl-substituted phenyl having 1 to 8 C atoms in the alkyl moiety, and q is 1 or 2, and $M^{q+}$ is $H^+$, $Ca^{2+}$, $Ni^{2+}$ or $Zn^{2+}$, and $X_1$ and $X_2$ are —O—.

Particularly preferred are compounds of the formula I wherein $R_1$ and $R_2$ are tert.-butyl, and $R_3$ is one of the groups II and III wherein n is 0, and $R_4$ is $C_1$–$C_{18}$-alkyl, phenyl or alkylsubstituted phenyl having 1 to 8 C atoms in the alkyl moiety, and q is 1 or 2, and $M^{q+}$ is $H^{30}$, $Co^{2+}$, $Ni^{2+}$ or $Zn^{2+}$, and $X_1$ and $X_2$ are oxygen.

Examples of compounds of the formula I are:

phosphorous acid monoester of 2,4-di-t.-butyl-phenyl 3,5-di-t.-butyl-4-hydroxy benzoate,
phosphorous acid monoester of octadecyl 3,5-di-t.-butyl-4-hydroxy benzoate,
phosphorous acid monoester of dodecyl 3,5-di-t.-butyl-4-hydroxy benzoate,
phosphorous acid monoester of octyl 3,5-di-t.-butyl-4-hydroxy benzoate,
phosphorous acid monoester of methyl 3,5-di-t.-butyl-4-hydroxy benzoate,
phosphorous acid monoester of 2,4-dimethyl-phenyl 3,5-di-t.-butyl-4-hydroxy-α-phenylacetate, and
phosphorous acid monoester of phenyl 3-t-octyl-5-t.-butyl-4-hydroxy-γ-phenylbutyrate.

The compounds of the formula I are produced in a manner known per se. The process comprises reacting a phenol of the general formula IV

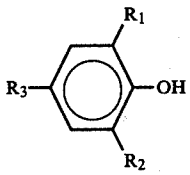

wherein $R_1$, $R_2$ and $R_3$ have the aforegiven meanings, optionally in the presence of a base, with a phosphorus (III) halide, optionally in an inert solvent. The reaction temperature can vary from 0° C. up to reflux temperature, e.g. about 130° C. The preferred temperature range is between 0 and 25° C. The phosphorus acid ester dihalide intermediately formed by this reaction is subsequently hydrolysed with water to a compound of the formula I. If hydrolysis is performed with a suitable metal hydroxide $M^{q+}(OH)_q$, the respective metal salts are obtained directly. A suitable phosphorus (III) halide is preferably phosphorus (III) chloride; however, the use of the corresponding fluoride, bromide or iodide is also possible. The reaction is preferably performed in the presence of a base which serves as HCl receiver. Organic nitrogen bases have proved particularly suitable, e.g. triethylamine, tributylamine, N,N-diethylaniline, pyridine or quinoline. There is preferably used, as a suitable metal hydroxide $M^{q+}(OH)_q$, an alkali metal hydroxide; the direct formation of the metal salts is however possible also with other cations, such as $Al^{3+}$. As solvent is advantageously used one which is able to dissolve phosphorus trihalides, for example ether, benzene, toluene, chloroform or carbon tetrachloride. It is however possible to perform the reaction without solvent.

The production of compounds of the formula IV is known.

Salts are formed most simply by reacting a compound of the formula I, wherein $M^{q+}$ is $H+$, with an alkali metal hydroxide; and reacting the resulting alkali metal salt with an alkaline-earth metal salt, a heavy metal salt or a transition metal salt, such as $NiCl_2.6H_2O$ or $CoCl_2$.

The compounds of the formula I wherein $R_4$ is hydrogen can be converted to salts by methods customary in the art, e.g. by neutralisation of the acid with a metal salt.

The $Ni^{2+}$ and $Co^{2+}$ compounds are distinguished by good dyesite properties for polyolefins, and particularly for polypropylene. These salts are very thermostable and display, even in the presence of sulphur-containing compounds, no discoloration, such as that frequently occurring in the case of other nickelcontaining compounds.

The light stabilisation properties are particularly pronounced with compounds in which n is 0.

The compounds of the formula I can be used according to the present invention as stabilisers for plastics to stabilise these against damage caused by the action of oxygen, heat and light. Examples of such plastics are the polymers listed in the German Offenlegungsschrift No. 2,456,864 on pages 12–14.

The stabilisation of polyolefins, styrene polymers and polyurethanes is of importance. Examples of these are polystyrene, styrene/butadiene/acrylonitrile copolymers, mixtures of polyolefins or of styrene polymers, polyurethanes, based on poly ethers or polyesters, in the form of lacquers, elastomers or foam plastics, and especially polyolefins such as 1. polymers derived from monounsaturated hydrocarbons, such as polyolefins, e.g. polyethylene, of low and high density, which can optionally be cross-linked, polypropylene, polyisobutylene, polymethylbutene-1 and polymethylphentene-1;
2. mixtures of the homopolymers mentioned under 1, such as mixtures of polypropylene and polyethylene, polypropylene and polybutene-1, or polypropylene and polyisobutylene; and
3. copolymers of the monomers from which the homopolymers mentioned under 1 are derived, such as ethylene/propylene copolymers, propylene/butene-1 copolymers, propylene/isobutylene copolymers, ethylene/butene-1 copolymers, and also terpolymers of ethylene and propylene with a diene, such as hexadiene, di-cyclopentadiene or ethylidenenorbornene.

The stabilisers are added to the plastics at a concentration of 0.01 to 5% by weight, relative to the weight of the material to be stabilised. There is preferably incorporated into the materials to be stabilised 0.03 to 1.5% by weight of the compounds of the formula I, relative to the weight of this material.

The incorporation can be effected after polymerisation, for example by mixing the compounds and, optionally, further additives into the melt by methods customary in the art, before or during moulding, or by applying the dissolved or dispersed compounds to the polymer, if need be with subsequent removal of the solvent by evaporation.

The new compounds can also be added in the form of a masterbatch, which contains these compounds for example at a concentration of 2.5 to 25% by weight, to the plastics to be stabilised.

In the case of crosslinked polyethylene, the compounds are added before crosslinking.

The invention thus also relates to the plastics which have been stabilised by the addition of 0.01 to 5% by weight of a compound of the formula I, which plastics can optionally also contain further known and customary additives. The plastics stabilised in this way can be used in a wide variety of forms, for example in the form of films, fibres, tapes or profiles, or as binders for lacquers, adhesives or cements.

The following are to be mentioned as examples of further additives together with which the stabilisers usable according to the invention may be employed: antioxidants, such as simple 2,6-dialkylphenols, derivatives of alkylated hydroquinones, hydroxylated thiodiphenyl ethers, alkylidene-bisphenols, O-N- and S-benzyl compounds, hydroxybenzylated malonates, hydroxybenzyl-aromatic compounds, s-triazine compounds, amides of β-(3,5 -di-tert.-butyl-4-hydroxyphenyl)-propionic acid, esters of β-(3,5-di-tert.-butyl-4-hydroxyphenyl)-propionic acid, esters of β-(5-tert.-butyl-4-hydroxy-3-methylphenyl)-propionic acid, esters of 3,5-di-tert.-butyl-4-hydroxyphenyl-acetic acid, acylaminophenols, benzyl-phosphonates and aminoaryl derivatives, UV absorbers and light stabilisers, such as 2-(2'-hydroxyphenyl)-benztriazoles, 2,4-bis(2'-hydroxyphenyl)-6-alkyl-s-triazines, 2-hydroxybenzophenones, 1,3-bis-(2'-hydroxybenzoyl)-benzenes, esters of optionally substituted benzoic acids and acrylates, and also nickel compounds, sterically hindered amines, oxalic acid diamides, metal deactivators, phosphites, compounds which break down peroxides, polyamide stabilisers, basic co-stabilisers, PVC stabilisers, nucleating agents or other additives, such as plasticisers, lubricants, emulsifiers, fillers, carbon black, asbestos, kaolin, talc, glass fibres, pigments, optical brighteners, flameproofing agents and antistatic agents.

Examples of further additives which can be employed together with the stabilisers to be used according to the invention can be found in the German Offenlegungsschrift No. 2,427,853 on pages 18–24.

The production and use of the compounds according to the invention are described in more detail in the following Examples.

EXAMPLE 1

Production of phosphorus acid monoester of 2',4'-di-t.-butylphenyl-3,5-di-t.-butyl-4-hydroxybenzoate A solution of 4.3 g of phosphorus (III) chloride in 50 ml of toluene is added dropwise to a solution of 13.2 g of 2',4'-di-t.-butylphenyl 3,5-di-t.-butyl-4-hydroxybenzoate and 3.2 g of triethylamine in 100 ml of toluene; and the reaction mixture is subsequently stirred for 12 hours at room temperature. After removal of the precipitate from triethylamine hydrochloride by filtration, the reaction solution is washed twice with 250 ml of water each time, and dried over sodium sulphate. Removal of the toluene by evaporation in vacuo and crystallisation of the residue from a toluene/ligroin mixture yield the substance given in the heading, in the form of colourless crystals having a melting point of 182°–183° C. (stabiliser 1).

Elementary analysis, $C_{29}H_{43}PO_5$ (502.63). calculated: 69.29% C, 8.62% H, 6.16% P. found: 69.32% C, 8.66% H, 6.23% P.

EXAMPLE 2

Production of the Ni salt of the phosphorus acid monoester of 2',4'-di-t.-butylphenyl-3,5-di-t.-butyl-4-hydroxybenzoate 10 ml of a 10 N sodium hydroxide solution is added to the suspension of 50.2 g (0.1 mole) of the phosphorus acid monoester of 2',4'-di-tert.-butyl-phenyl 3,5-di-tert.-butyl-4-hydroxybenzoate in 800 ml of water. There is formed a clear solution, to which is added dropwise, at room temperature, 12.5 g of nickel chloride hexahydrate (0.0525 mole) dissolved in 50 ml of water. There precipitates out a light-green precipitate which is filtered off and washeed with water, and subsequently dried at 60° C. under 11 mm Hg. The product thus obtained is the Ni-(II)-salt of the phosphorus acid monoester of 2,4-di-tert.-butyl-phenyl 3,5-di-tert.-butyl-4-hydroxybenzoate in the form of a light-green powder which melts at 220° C. with decomposition (stabiliser 2).

Elementary analysis $C_{58}H_{86}P_2O_{10}Ni$ (1061.9). calculated: 5.5 % Ni, 5.8% P. found: 5.4% Ni, 5.6% P.

EXAMPLE 3

100 parts of polyproylene powder (Moplen, fibre grade, Montedison) are homogenised with 0.2 part of octadecyl β-(3,5-di-tert.-butyl-4-hydroxyphenyl)-propionate and 0.25 part of a stabiliser given in the following Table for 10 minutes at 200° C. in a Brabender plastograph. The mixture thus obtained is removed as quickly as possible from the kneader and pressed in a toggle press to form 2–3 mm thick sheets. A part of the sheet material obtained is cut out and pressed between two highly polished sheets in a hand-hydraulic laboratory press for 6 minutes at 260° C. under a pressure of 12 tons to obtain a 0.5 mm thick sheet, which is immediately quenched in cold water. Under exactly identical conditions there is produced from this 0.5 mm thick sheet the 0.1 mm thick test sheet. From this are then stamped sections each 60 × 44 mm, and these are exposed to light in the Xenotest 150. At regular intervals of time, these specimens are removed from the exposure apparatus and tested in an IR spectrophotometer for their carbonyl content. The increases of the carbonyl extinction on exposure is a measure for the photooxidative degradation of the polymer (see L. Balaban et al., J. Polymer Sci. Part C, 22, 1059–1071 (1969); J.F. Heacock, J. Polymer Sci. Part A-1, 22, 2921–34 (1969); D.J. Carlsson and D.M. Wiles, Macromolecules 2, 587–606 (1969)) and from experience is associated with a deterioration of the mechanical properties of the polymer.

The time to reach a carbonyl extinction of about 0.300 is taken as a measure of the protective action.

The results are summarised in the Table.

TABLE

| Stabiliser | Hours | Stabilisation factor |
| --- | --- | --- |
| No. 1 | 4 800 | 4.6 |
| none | 1 040 | |

EXAMPLE 4

1000 parts of polypropylene powder [melt index 1.5 g/10 minutes (230° C. 2160 g)] are mixed in a drum mixer with 1 part of pentaerythritol tetrakis-β-(3,5-di-tert.-butyl-4-hydroxyphenyl)-propionate, 3 parts of dilaurylthiodipropionate (DLTDP) and 5 parts of a light stabiliser given in the following Table, and the mixture is subsequently homogenised in a Brabender plastograph at 200° C. for 10 minutes. The polymer mixture is then pressed in a heated press for 6 minutes at 300° C. to form 1 mm thick sheets. A visual assessment of the test samples with regard to their discoloration gives the following results:

| Stabiliser | Result after pressing at 300° C. |
| --- | --- |
| No. 2 | no discoloration |

We claim:

1. A compound of the general formula I

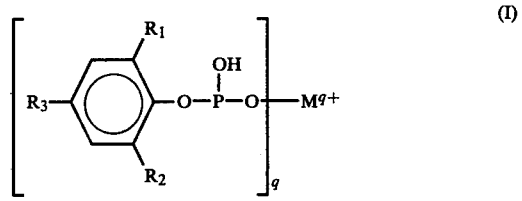

wherein
$R_1$ and $R_2$ independently of one another are $C_1$–$C_8$-alkyl, $C_5$–$C_8$-cycloalkyl or $C_7$–$C_9$-aralkyl,
$R_3$ is a group of the formula II

wherein n is 0 to 6,
$R_4$ is $C_1$–$C_{24}$-alkyl, phenyl, or alkyl-substituted phenyl having 1–12 C atoms in the alkyl moiety,
q is 1, 2 or 3,
$M^{q+}$ is $H^+$ or a mono-, bi- or trivalent metallic cation.

2. A compound according to claim 1 of the formula I, wherein $R_1$ and $R_2$ independently of one another are $C_4$–$C_8$-alkyl, and $R_3$ is a group of the formula II wherein n is 0 to 3, and $R_4$ is $C_1$–$C_{18}$-alkyl, phenyl, or alkyl-substituted phenyl having 1 to 8 C atoms in the alkyl moiety, and q is 1, 2 or 3, $M^{q+}$ is $H^+$, $Na^+$, $K^+$, $Mg^{2+}$, $Ca^{2+}$, $Cr^{3+}$, $Co^{2+}$, $Ni^{2+}$, $Zn^{2+}$, $Al^{3+}$ or $Sn^{2+}$.

3. A compound according to claim 1 of the formula I, wherein $R_1$ and $R_2$ independently on one another are $C_4$-alkyl or $C_8$-alkyl and $R_3$ is a group of the formula II wherein n is 0 to 2, and $R_4$ is $C_1$–$C_{18}$-alkyl, phenyl, or alkyl-substituted phenyl having 1 to 8 C atoms in the alkyl moiety, and q is 1 or 2, $M^{q+}$ is $H^+$, $Ca^{2+}$, $Ni^{2+}$ or $Zn^{2+}$.

4. A compound according to claim 1 of the formula I, wherein $R_1$ and $R_2$ are tert.-butyl, and $R_3$ is of the group II wherein n is O, and $R_4$ is $C_1$–$C_{18}$-alkyl, phenyl, or alkylsubstituted phenyl having 1 to 8 C atoms in the alkyl moiety, and q is 1 or 2, and $M^{q+}$ is $H^+$, $Co^{2+}$ or $Ni^{2+}$.

5. A polymer containing a compound of the formula I according to claim 1.

6. A compound of the formula I according to claim 1, which is the phosphorus acid monoester of 2',4'-di-t.-butylphenyl-3,5-di-t.-butyl-4-hydroxybenzoate.

7. A compound of the formula I according to claim 1, which is the Ni-salt of the phosphorus acid monoester of 2',4'-di-t.-butylphenyl-3,5-di-t.-butyl-4-hydroxybenzoate.

* * * * *